United States Patent
Joshi et al.

(10) Patent No.: US 7,615,036 B2
(45) Date of Patent: Nov. 10, 2009

(54) DEVICE AND METHOD FOR WOUND THERAPY

(75) Inventors: Ashok V. Joshi, Salt Lake City, UT (US); John Howard Gordon, Salt Lake City, UT (US); Sai Bhavaraju, Salt Lake City, UT (US); Troy C. Dayton, Syracuse, UT (US)

(73) Assignee: Kalypto Medical, Inc., Mendota Heights, MN (US)

( * ) Notice: Subject to any disclaimer, the term of this patent is extended or adjusted under 35 U.S.C. 154(b) by 58 days.

(21) Appl. No.: 11/432,855

(22) Filed: May 11, 2006

(65) Prior Publication Data

US 2007/0265585 A1 Nov. 15, 2007

(51) Int. Cl.
*A61M 1/00* (2006.01)
(52) U.S. Cl. .............. 604/313; 604/304; 604/305; 604/306; 604/307; 604/315; 604/316; 604/317; 604/541; 604/543; 602/42; 602/43; 602/46
(58) Field of Classification Search .......... 604/304–307, 604/313, 315, 316, 317, 541, 543; 602/42, 602/43, 46
See application file for complete search history.

(56) References Cited

U.S. PATENT DOCUMENTS

| | | | |
|---|---|---|---|
| 2,568,933 A | | 9/1951 | Robbins |
| 3,572,340 A | | 3/1971 | Lloyd et al. |
| 4,217,894 A | * | 8/1980 | Franetzki .............. 604/84 |
| 4,534,356 A | * | 8/1985 | Papadakis ............ 600/358 |
| 4,655,766 A | | 4/1987 | Theeuwes et al. |
| 4,969,880 A | | 11/1990 | Zamierowski |
| 4,979,944 A | * | 12/1990 | Luzsicza ............. 604/118 |
| 5,167,613 A | | 12/1992 | Karami et al. |
| 5,266,928 A | | 11/1993 | Johnson |
| 5,279,608 A | * | 1/1994 | Cherif Cheikh ........ 604/892.1 |
| 5,636,643 A | | 6/1997 | Argenta et al. |
| 5,645,081 A | | 7/1997 | Argenta et al. |
| 5,785,688 A | | 7/1998 | Joshi et al. |

(Continued)

FOREIGN PATENT DOCUMENTS

DE 20 2005 019 670 U1 4/2006

(Continued)

OTHER PUBLICATIONS

Argenta, Louis C., et al., "Vacuum-Assisted Closure: A New Method for Wound Control and Treatment; Clinical Experience", *Ann Plas Surg* 1997;38:563-577, (Dec. 10, 1996),563-577.

(Continued)

*Primary Examiner*—Michele Kidwell
*Assistant Examiner*—Ilya Y Treyger
(74) *Attorney, Agent, or Firm*—Factor & Lake

(57) ABSTRACT

A wound therapy device is disclosed. The wound therapy device may include a housing for covering at least a portion of a wound and for sealing to a body surface of a patient. The housing may also include a liquid-retention chamber for retaining liquid therein and a vacuum connection for coupling to a vacuum source. The vacuum connection may be in gaseous communication with the liquid-retention chamber. The vacuum connection may be separated from the liquid-retention chamber by a liquid barrier.

30 Claims, 6 Drawing Sheets

U.S. PATENT DOCUMENTS

| | | | |
|---|---|---|---|
| 5,868,933 | A | 2/1999 | Patrick et al. |
| 5,964,723 | A | 10/1999 | Augustine |
| 6,135,116 | A | 10/2000 | Vogel et al. |
| 6,142,982 | A | 11/2000 | Hunt et al. |
| 6,398,767 | B1 | 6/2002 | Fleischmann |
| 6,458,109 | B1 | 10/2002 | Henley et al. |
| 6,471,982 | B1 * | 10/2002 | Lydon et al. ............... 424/443 |
| 6,491,684 | B1 | 12/2002 | Joshi et al. |
| 6,553,998 | B2 | 4/2003 | Heaton et al. |
| 6,648,862 | B2 | 11/2003 | Watson |
| 6,673,028 | B1 | 1/2004 | Argenta et al. |
| 6,685,681 | B2 | 2/2004 | Lockwood et al. |
| 6,695,823 | B1 | 2/2004 | Lina et al. |
| 6,752,794 | B2 | 6/2004 | Lockwood et al. |
| 6,764,462 | B2 | 7/2004 | Risk et al. |
| 6,767,334 | B1 | 7/2004 | Randolph |
| 6,814,079 | B2 | 11/2004 | Heaton et al. |
| 6,824,533 | B2 | 11/2004 | Risk et al. |
| 6,855,135 | B2 | 2/2005 | Lockwood et al. |
| 6,856,821 | B2 | 2/2005 | Johnson |
| 6,936,037 | B2 | 8/2005 | Bubb et al. |
| 6,951,553 | B2 | 10/2005 | Bubb et al. |
| 6,994,702 | B1 | 2/2006 | Johnson |
| 7,004,915 | B2 | 2/2006 | Boynton et al. |
| 2001/0029956 | A1 | 10/2001 | Argenta et al. |
| 2002/0115952 | A1 | 8/2002 | Johnson et al. |
| 2002/0120185 | A1 | 8/2002 | Johnson |
| 2002/0143286 | A1 | 10/2002 | Tumey |
| 2002/0183702 | A1 | 12/2002 | Henley et al. |
| 2003/0014022 | A1 | 1/2003 | Lockwood et al. |
| 2003/0040687 | A1 | 2/2003 | Boynton et al. |
| 2003/0050594 | A1 | 3/2003 | Zamierowski |
| 2003/0212357 | A1 | 11/2003 | Pace |
| 2003/0225347 | A1 | 12/2003 | Argenta et al. |
| 2004/0019342 | A1 | 1/2004 | Nagasuna et al. |
| 2004/0030304 | A1 | 2/2004 | Hunt et al. |
| 2004/0039391 | A1 | 2/2004 | Argenta et al. |
| 2004/0073151 | A1 | 4/2004 | Weston |
| 2004/0122434 | A1 | 6/2004 | Argenta et al. |
| 2004/0127863 | A1 | 7/2004 | Bubb et al. |
| 2004/0225208 | A1 | 11/2004 | Johnson |
| 2005/0004534 | A1 | 1/2005 | Lockwood et al. |
| 2005/0010153 | A1 | 1/2005 | Lockwood et al. |
| 2005/0028828 | A1 | 2/2005 | Heaton et al. |
| 2005/0070835 | A1 * | 3/2005 | Joshi ............... 602/41 |
| 2005/0148913 | A1 | 7/2005 | Weston |
| 2005/0203452 | A1 | 9/2005 | Weston et al. |
| 2005/0222527 | A1 | 10/2005 | Miller et al. |
| 2005/0222528 | A1 | 10/2005 | Weston |
| 2005/0222544 | A1 | 10/2005 | Weston |
| 2005/0261615 | A1 | 11/2005 | Weston |
| 2005/0261642 | A1 | 11/2005 | Weston |
| 2006/0015087 | A1 | 1/2006 | Risk et al. |
| 2006/0025727 | A1 | 2/2006 | Boehringer et al. |
| 2006/0041247 | A1 | 2/2006 | Petrosenko et al. |
| 2006/0100594 | A1 | 5/2006 | Adams et al. |
| 2006/0116620 | A1 | 6/2006 | Oyaski |

FOREIGN PATENT DOCUMENTS

| | | |
|---|---|---|
| EP | 0708620 | 5/2003 |
| EP | 1088569 | 8/2003 |
| FR | 1163907 | 10/1956 |
| WO | WO 90/11795 | 10/1990 |
| WO | WO 00/59424 | 10/2000 |
| WO | WO-01/34223 | 5/2001 |
| WO | WO 01/34223 * | 5/2001 |
| WO | WO 01/85248 | 11/2001 |
| WO | WO 03/092620 | 11/2003 |
| WO | WO-2005/025666 | 3/2005 |

OTHER PUBLICATIONS

Chintamani, et al., "Half versus full vacuum suction drainage after modified radical mastectomy for breast cancer- a prospective randomized clinical trial", *Research Article*, (Jan. 27, 2005), 1-5.

Davydov, Yu A., et al., "Concepts for Clinical Biological Management of the Wound Process in the Treatment of Purulent Wounds Using Vacuum Therapy", *The Kremlin Papers: Perspectives in Wound Care. Russian Journal: Vestnik Khirurgii. BlueSky Publishing*. La Costa, California., (2004), 15-17.

Davydov, Yu A., et al., "The Bacteriological and Cytological Assessment of Vacuum Therapy of Purulent Wounds", *The Kremlin Papers: Perspectives in Wound Care. Russian Journal: Vestnik Khirurgii. BlueSky Publishing*. La Costa, California., (2004), 11-14.

Davydov, Yu A., et al., "Vacuum Therapy in the Treatment of PUrulent Lactation Mastitis", *The Kremlin Papers: Perspectives in Wound Care. Russian Journal: Vestnik Khirurgii. BlueSky Publishing*. La Costa, California., (2004),5-7.

De Lange, M.Y. , et al., "Vacuum-Assisted Closure: Indications and Clinical Experience", *Eur J Plast Surg* (2000) 2;178-182, (Feb. 9, 2000),178-182.

Health Technology, Literature R., "Vacuum Assisted Closure Therapy for Wound Care", *Health Technology Literature Review*, (Dec. 2004),3-59.

Khirugii, Vestnik , "A Collection of Published Studies Complementing the Research and Innovation of Wound Care", *The Kremlin Papers, Perspectives in Wound Care; Russian Medical Journal; Vestnik Khirugii, Blue Sky Publishing*, (2004),2-17.

Kostiuchenok, B. M., et al., "The Vaccuum Effect in the Surgical Treatment of Purulent Wounds", *The Kremlin Papers: Perspectives in Wound Care. Russian Journal: Vestnik Khirurgii. BlueSky Publishing*. La Costa, California., (2004),3-4.

Morykwas, Michael J., et al., "Vacuum-Assisted Closure: A New Method for Wound Control and Treatment: Animal Studies and Basic Foundation", *Ann Plast Surg* 1997;38:553-562, (Dec. 10, 1996),553-562.

Usupov, Y. N., et al., "Active Wound Drainage", *The Kremlin Papers: Perspectives in Wound Care. Russian Journal: Vestnik Khirurgii. BlueSky Publishing*. La Costa, California., (2004),8-10.

Venturi, Mark L., "Mechanisms and Clinical Applications of the Vacuum-Assisted Closure (VAC) Device", *Am J Clin Dermatol* 2005; 6 93); 185-194, Review Article,(2005),185-194.

PCT International Search Report of PCT/US2007/011321, International Filing Date May 10, 2007, Applicant is Iasis Medical, LLC.

Written Opinion of the International Searching Authority of PCT International Search Report of PCT/US2007/011321, International Filing Date May 10, 2007, Applicant is Iasis Medical, LLC.

International Search Report of International Application No. PCT/NL2004/000565 consisting of 5 pages, Jul. 29, 2005.

International Search Report of International Application No. PCT/GB00/01566 consisting of 2 pages, Sep. 25, 2000.

International Search Report of International Application No. PCT/GB00/04278 consisting of 2 pages, Feb. 22, 2001.

International Search Report of International Application No. PCT/US2007/011278 consisting of 6 pages, May 11, 2006.

Written Opinion of the International Search Report of PCT/US2007/011278 consisting of 7 pages, Dec. 11, 2007.

U.S. Appl. No. 11/610,458, Dec. 13, 2006.

* cited by examiner

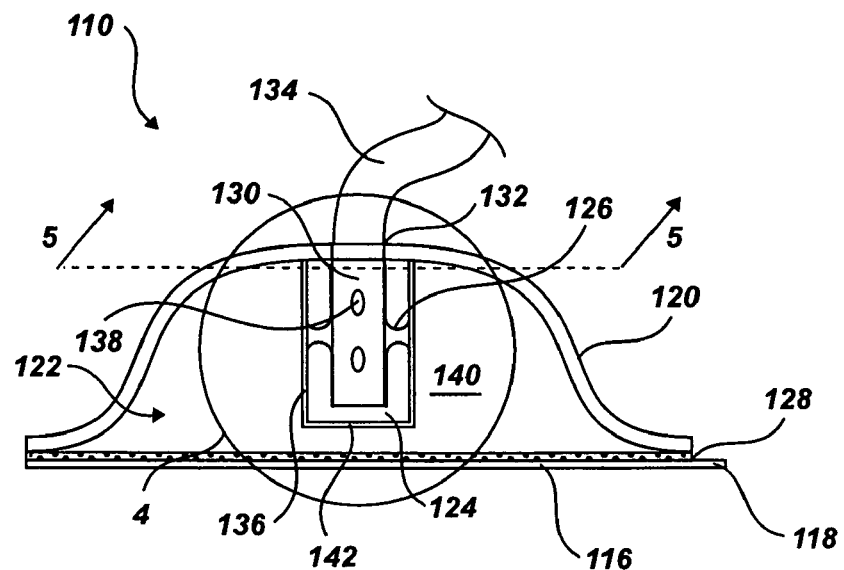
Fig. 3
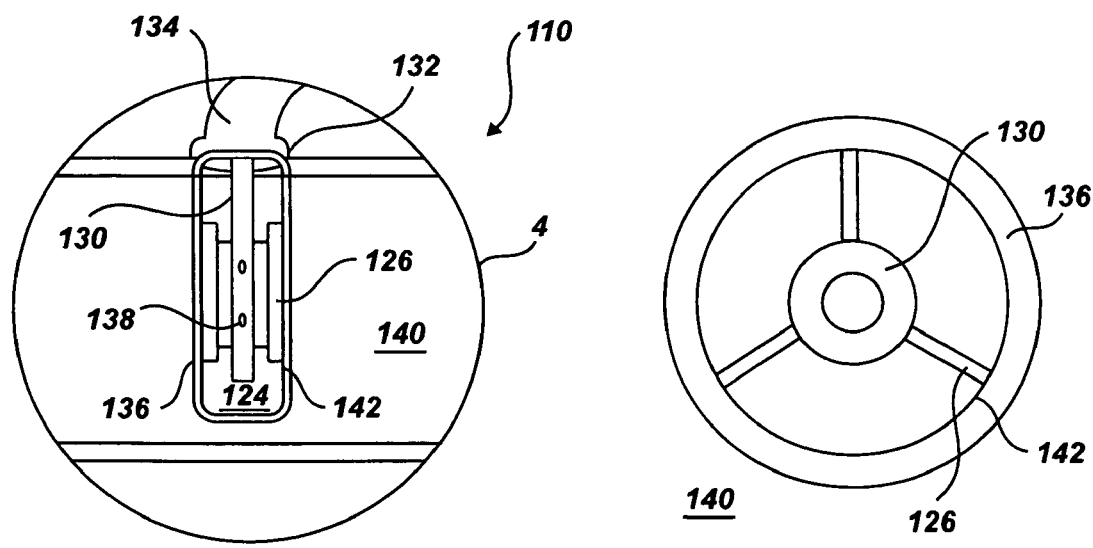
Fig. 4
Fig. 5

DEVICE AND METHOD FOR WOUND THERAPY

TECHNICAL FIELD

The disclosure relates in general to a device and method for wound therapy that is capable of treating a variety of chronic and acute wound types, including, but not limited to, infection wounds, venous ulcers, arterial ulcers, diabetic ulcers, burn wounds, post amputation wounds, surgical wounds, and the like. Specifically, the present disclosure is related to wound treatment devices and methods that utilize negative pressure therapy.

BACKGROUND

Negative pressure therapy has been one tool used for the treatment of a variety of wounds by practitioners in the art. Conventional devices are generally large in size and often require the use of complicated equipment such as suction pumps, vacuum pumps and complex electronic controllers. Other associated equipment may include wound liquid/exudate collection canisters, liquid transporting conduits, and pressure regulators/transducers/sensors. As a result, such devices may be bulky, power intensive, relatively costly and substantially non-disposable. Furthermore, the complexity of conventional devices requires steady patient supervision and that initial placement and any changing of the devices be conducted by a physician or nurse. At present, a typical cost for the use of these devices is on the order of about $100 per day per patient.

The rising costs of healthcare and of medical devices place pressure on patients and care providers alike to seek out solutions that allow use by a patient in-home, with less supervision. Furthermore, patients continue to demand devices that are more easily portable to allow travel and mobility.

BRIEF SUMMARY

The present disclosure provides a self-integrated wound therapy device for providing negative pressure therapy to a wound. In one embodiment, the device may include a housing to cover at least a portion of a wound. The device may also include a liquid-retention chamber and a vacuum connection for coupling to a vacuum source. The vacuum connection may be in gaseous communication with the liquid-retention chamber. The vacuum connection may be separated from the liquid-retention chamber by a liquid barrier. The wound therapy device may also include a seal to seal the housing to a body surface of a patient.

The vacuum connection in some embodiments may be coupled to a micro-vacuum pump that may be optionally located within or adjacent to the housing. In other embodiments, the vacuum connection may comprise a vacuum port that may be coupled to a vacuum source located at some distance from the housing.

In other embodiments, the wound therapy device may be modular in nature, optionally including a wound interface module, a liquid-retention module and a vacuum pump module. Each module of the wound therapy device may be optionally separately replaceable.

BRIEF DESCRIPTION OF THE SEVERAL VIEWS OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

FIG. 3 is a side cross-sectional view of another embodiment of a wound healing device including a droplet gap as a liquid barrier.

FIG. 4 is a magnified view of the droplet gap of the device of FIG. 3.

FIG. 5 is a top cross-sectional view of the droplet gap of the device of FIG. 3.

DETAILED DESCRIPTION

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

Figure 1:
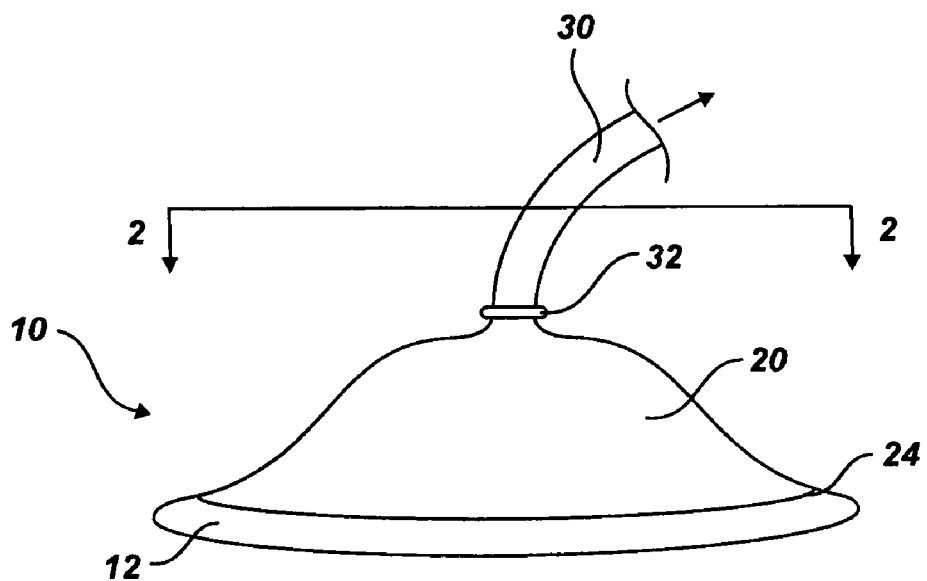
FIG. 1 is a perspective view of one embodiment of a wound healing device.

Referring now to the enclosed figures and in particular to FIG. 1, a wound therapy device 10 is shown in a perspective view attached to a body surface of a patient at least partially encompassing a wound. The device 10 includes a housing 20 that defines an internal space. In one embodiment, the housing 20 is rigid or semi-rigid. This may prevent the housing 20 from significantly collapsing upon application of a vacuum. The housing 20 may also be made of a flexible barrier or surface wrap supported by customizable rigid or semi-rigid structural supports (not shown) that provide support to the housing 20 allowing the maintenance of vacuum within the housing 20. The flexible barrier/surface wrap may be a thin polyurethane film with a dermal compatible adhesive supported by structural foam that also serves as a liquid-retention chamber. By way of example, these structural supports can be made from rigid or semi-rigid plastics and foams, e.g., polystyrene, polyester, polyether, polyethylene, silicone, neoprene and the like.

In one embodiment, the housing 20 is semi-permeable. The exemplary semi-permeable housing may be substantially impermeable to liquids but somewhat permeable to water vapor and other gases while capable of maintaining a negative pressure underneath the housing 20 upon application of a vacuum. By way of example, the housing material may be constructed of polyurethane or other semi-permeable material such as those sold under the Tegaderm® brand. In one embodiment the housing 20 may have a water vapor transmission rate ("WVTR") of about 836 grams/m$^2$/day or more. However, in other embodiments the WVTR may be less than about 836 grams/m$^2$/day. In yet other embodiments, the housing material may be substantially impermeable to both liquids and gases (including water vapor).

When the device 10 is placed on a patient and activated, or attached to an external pump via a vacuum connection 30, through adapter 32, the device 10 delivers negative pressure to the wound. The device 10 is generally attached to the body surface of a patient using one of a variety seals known in the art, such as, in one embodiment, a housing seal 24. In some adaptations, however, the device 10 may optionally include a flexible barrier 12 used to secure the device 10 to the patient. Furthermore, in some embodiments a micro-vacuum pump may be used internal to or adjacent the housing 20.

Figure 2:
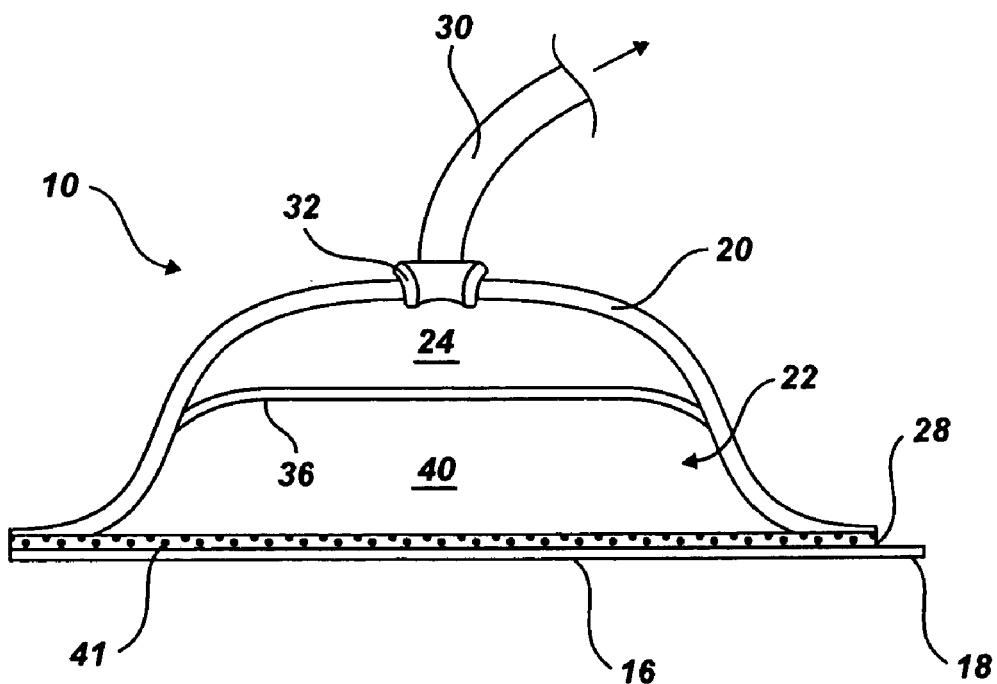
FIG. 2 is a side cross-sectional view of the wound healing device of FIG. 1, including a port or valve as a vacuum source.

FIG. 2 is a side cross-sectional view of the device 10 of FIG. 1 taken along plane 2-2 of FIG. 1. The view of FIG. 2 illustrated the internal construction and organization of this embodiment of the wound therapy device 10. Device 10 is thus shown to include a rigid or semi-rigid housing 20 which defines an internal space 22. In device 10, this internal space 22 is further subdivided into a vacuum chamber 24 and a liquid-retention chamber 40 separated by a liquid barrier 36. The vacuum connection 30 is illustrated to be, in this embodiment, an adaptor 32 that allows the attachment of an external vacuum source (not shown) in the form of a vacuum pump or other source known to one of ordinary skill in the art. The vacuum connection 30 is in gaseous communication with the vacuum chamber 24, and thus with the liquid-retention chamber 40 via the liquid barrier 36. The vacuum connection 30 may be coupled to a micro-vacuum pump or another source of negative pressure adjacent the device, or an external vacuum pump.

In one embodiment, the vacuum connection 30 may be coupled to an osmotic or electro-osmotic pump adjacent or internal to the housing. An osmotic pump involves imbibing water or another driving fluid. The pump may consist of a salt chamber and a liquid chamber. The salt and water chambers are separated by a semi-permeable membrane that is substantially permeable to water but substantially impermeable to salt. Water imbibes osmotically into the salt chamber creating a vacuum or partial vacuum. Materials other than salt and water can be used to cause a liquid to vacate a space in order to create a vacuum or partial vacuum. The semi-permeable or osmotic membrane may be any cation or anion membrane in communication with the liquid retention chamber. Many osmotic membranes are available commercially, any of which could be included in the present invention.

In one embodiment, electro-osmotic pump may be used to create a vacuum or partial vacuum. A selectively permeable membrane may be positioned at or near the vacuum chamber which enables a fluid to osmotically diffuse thereby creating a vacuum, partial vacuum, or negative pressure in the vacuum chamber. In operation, the electro-osmotic pump is actuated, whereupon an electrical circuit is complete and a voltage is applied from power source across a pair of electrodes, which causes an electrode reaction to take place and water or other fluid to be extracted to create the vacuum or partial vacuum.

In these alternative embodiment, the method of treating the wound may include the steps of providing housing having a cavity, positioning at least a portion of the wound within a cavity of the housing, and the steps of first filling the cavity with fluid such as water removing the fluid (water) from the cavity and then using osmotic or electro-osmotic cell and thereby generating a controlled vacuum or partial vacuum within the cavity or housing.

The liquid barrier 36 serves to prevent travel of liquid from the liquid-retention chamber 40 to the vacuum connection 30. As such, it may comprise any of a large family of suitable technologies that prevent travel of liquid from the liquid-retention chamber 40 into the vacuum chamber 24 while allowing gas flow, and thus transmission of negative pressure provided through the vacuum connection 30. As such, the liquid barrier 36 may include a porous hydrophobic film, a porous hydrophobic structure, a droplet gap, or a labyrinth. Examples of porous hydrophobic films include, but are not limited to, porous and microporous polytetrafluoroethylene, polypropylene, polyethylene, or fibrous layers of each and combinations thereof. For example, porous hydrophobic films sold under the Gore-Tex® brand may be suitable. Other technologies that allow gas flow but prevent liquid flow may also be used as suitable liquid barriers 36 as would be apparent to those having skill in the art with the aid of the present disclosure.

In the device 10 of FIG. 2, the liquid barrier 36 is a porous hydrophobic film configured to allow gas flow while at least substantially blocking liquid flow. Thus, when a vacuum source (not shown) is attached to the adapter 32 of the vacuum connection 30, negative pressure is supplied/transmitted through the vacuum chamber 24 into the liquid-retention chamber 40, drawing liquid from the wound site into the liquid-retention chamber 40. The liquid-retention chamber 40 may additionally include structures and/or substances to assist in retaining the liquid drawn into the chamber 40. Such structures and/or substances may include sponges; wicking fibers, fabrics, or gauzes; super-absorbent material including super-absorbent polymers that form gels; absorbent foams; gelling agents; packing; and other structures an/or substances having similar features that are known to one of ordinary skill in the art. Such porous structures or materials permit the flow of gas to allow the vacuum to be applied to the wound while absorbing and retaining liquid drawn out of the wound. In some embodiments, the liquid absorbing structures or agents may be antimicrobial in nature or may include antimicrobial agents.

Thus, in operation, the device 10 may be applied to a wound site of a patient like a patch, wherein a vacuum source coupled to the vacuum connection 30, provides negative pressure to the wound. Prior to use, the device 10 may be packaged to prevent contamination. Such packaging could be a bag or envelope, or could include the use of an optional protective seal 16, with an optional pull tab 18 that is removed from the device prior to placement on the patient. During application of negative pressure to the wound site, liquid is drawn into the liquid-retention chamber 40 and held within the liquid-retention chamber 40, being prevented from further travel by the liquid barrier 36.

The housing 20 of the devices 10 disclosed may be produced out of any suitable material known to one of ordinary skill in the art, including, without limitation, rubbers, including polyurethane, and dense plastics such as, but not limited to, polypropylene, polyvinyl chlorides, polyethylene, acrylonitrile-based copolymer, such as those sold under the Barex® brand, polyester, nylon, polychlorotrifluoroethylene, fluoropolymer, polytetrafluoroethylene, such as those sold under the Teflon® brand, or combinations thereof and similar materials. The housing 20 may be a rigid or semi-rigid structure generally surrounding the liquid-retention chamber 40 and the vacuum chamber 24, and substantially retains its size and structure during the application of negative pressure, thus allowing a vacuum to be held within the housing 20.

Alternatively, the housing 20 may be made of a flexible barrier supported by customizable rigid or semi-rigid structural supports that provide support to the housing 20 allowing the maintenance of vacuum within the housing 20. The housing 20 may also be made of a flexible barrier or a surface wrap, such as a thin polyurethane film with a dermal compatible adhesive, supported by structural foam that also serves as a liquid-retention chamber. These structural supports may be constructed from rigid or semi-rigid plastics and foams (e.g., polystyrene, polyester, polyether, polyethylene, silicone or neoprene).

The housing 20 of the devices 10 disclosed may additionally contain a wound interface layer 41 in direct contact with the wound and may comprise single or multiple layers. The wound interface 41 may be either placed directly inside the wound or over the wound. The wound interface 41 may serve many functions such as being a layer that allows supply of vacuum to the wound while allowing easy and unpainful removal from the wound site during dressing change, e.g., degradable copolymer foil, such as those sold under the Topkin® brand, or a layer that provides beneficial bioagents in the form of specialized dressings such as dermal regeneration templates (e.g., those sold under the Integra® brand), bioabsorbable gels, foams and barriers that prevent tissue adhesion (e.g., those sold under the Incert® brand), a skin substitute (e.g., those sold under the BioFill® brand), a layer for selectively maintaining moisture at the wound site (e.g., those sold under the Alevyn® brand), a layer that is angiogenic (e.g., those sold under the Theramers® brand), and/or a layer that is antimicrobial. The wound interface 41 may take a variety of forms including but not limited to a sheet, foam, gel, gauze or a porous matrix.

In some specific embodiments, the housing 20 may further include a pressure relief valve (not shown). Such a valve may additionally include an inflow filter to prevent entry of contaminants into the device 10, and thus to further protect the wound site. In still other embodiments, the device 10 may include a fill indicator. The device 10 may additionally include an overflow valve such as a float valve for the vacuum connection to prevent transmission of liquid into the vacuum source. The wound healing device 10 may also alternatively include a sensor to detect the pressure or oxygen level over the wound and within the cavity.

The housing 20 of the device 10 may be adapted to be sealed to a body surface of a patient. In some embodiments, this sealing may occur simply as a result of placing the housing 20 against the body surface and drawing a vacuum within the device 10. Adhesives, gaskets, and other sealing technologies known to one of ordinary skill in the art may also be used as a seal 28 including the use of adhesive backed thin polyurethane films. Other suitable seals are known to those of ordinary skill in the art and may be used with the embodiments disclosed. As illustrated in FIG. 1, the device may optionally, in some embodiments, be used with an over wrap to further protect and/or seal the device 10.

Referring next to FIG. 3, another embodiment of a wound therapy device 110 is shown from a side cross-sectional view analogous to that of FIG. 2. The wound therapy device 110 of FIG. 3 includes a housing 120 and a vacuum passage 130. In the device 110 of FIG. 3, the vacuum passage 130 is a port 132 adapted to receive an external vacuum source 134 in a sealed manner, such that the vacuum source 134 may apply a negative pressure to the device 110. In alternative embodiments, the vacuum source 134 may be adjacent to and internal or external to the housing 120. In exemplary device 110, the vacuum source 134 may be shared between a series of devices 110 on a single patient, or between several patients since no liquid passes into the vacuum connection 134 by the devices 110. The device 110 may optionally include a pressure sensor (not shown) to measure and indicate when application of the vacuum source 134 is needed to maintain pressure at a therapeutic level, such as, e.g., 75-80 mmHg vacuum.

As with the device 10 of FIGS. 1 and 2, the wound therapy device 110 of FIG. 3 may include a liquid-retention chamber 140 and a vacuum chamber 124. In this embodiment, the vacuum chamber 124 itself serves as a liquid barrier 136, acting as a "droplet gap" unable to be traversed by liquids drawn into the liquid retention chamber 140. More specifically, the vacuum chamber 124 may be a cylindrically-shaped void within the internal space 122 of the housing 120, which, due to its size, prevents liquid from traveling from the liquid-retention chamber 140 into the vacuum passage 130. The vacuum passage 130 may extend into the vacuum chamber 124, and may include at least one orifice 138. The housing 120 may also include internal supports 126 that extend between the vacuum passage 130 and the perimeter 142 of the liquid-retention chamber 140 to maintain proper distance between the vacuum passage 130 and the liquid-retention chamber 140.

The wound therapy device of FIGS. 1 and 2 could be modified to take advantage of the droplet gap principle illustrated in FIG. 3 simply by omitting the liquid barrier 36, so long as the housing 20 is sufficiently rigid to preserve the vacuum chamber 24, preventing contact between the vacuum connection 30 and the liquid-retention chamber 40.

Referring again to FIG. 3, the device 110 may optionally include a liquid barrier 136 in the form of a porous hydrophobic membrane positioned about the perimeter 142 of the liquid-retention chamber 140. Without being limited to any one theory, it is thought that inclusion of such a physical barrier may increase the orientation independence of the device 110.

FIG. 4 is a detail view of the vacuum chamber 124 and liquid barrier 136 of the device 110 of FIG. 3 showing the contents of circle 4 of FIG. 3. As depicted, internal supports 126 structurally locate the vacuum passage 130 within the vacuum chamber 124.

The exemplary structure, shape, and construction of the vacuum chamber 124 of the device 110 is further illustrated in FIG. 5, which is a cross-sectional view of the wound therapy device 110 of FIGS. 3 and 4 taken along plane 5-5 of FIG. 3. Internal supports 126 extend between the vacuum passage 130 and the perimeter 142 to maintain proper distance between the vacuum passage 130 and the liquid-retention chamber 140. In FIG. 5, the vacuum chamber 124 is illustrated to have a cylindrical profile. It should be noted that variation of the size, volume, or shape of the vacuum chamber 124 is within the skill of one of ordinary skill in the art. Thus, elliptical, rectangular, and other shapes, without limitation, are considered to be within the scope of the present disclosure.

Figure 6:
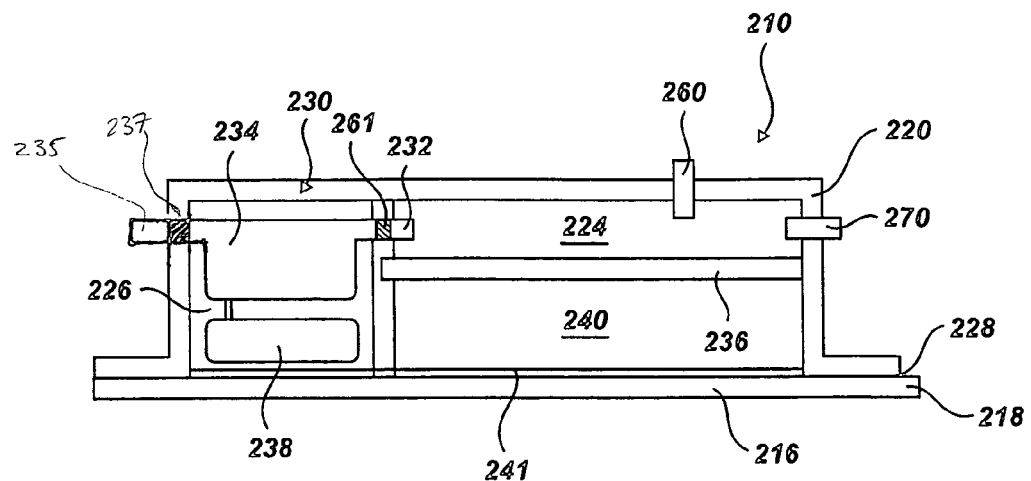
FIG. 6 is a side cross-sectional view of another embodiment of a wound healing device including an internal vacuum pump as the vacuum source.

Referring next to FIG. 6, another embodiment of the wound therapy patch device 210 is shown in a side cross-sectional view analogous to that of FIG. 2. The device 210 of FIG. 6, like those previously illustrated, includes a housing 220 that encloses an internal space. This embodiment of the wound therapy device 210, however, is configured to include a negative pressure source 230, including a vacuum source 234 and a supply coupling 232 that supplies negative pressure to the vacuum chamber 224. The vacuum source 234 is operably coupled to a power source 238 which together may be internal to the device 210 as illustrated. Further, although the vacuum source 234 and power source 238 are illustrated to be internal to the housing 220, in an auxiliary chamber 226 in FIG. 6, it should be understood that such apparatus may be located outside of the housing 220, or may alternatively be placed in a modular portion of the device 210 which may be removed and replaced as needed.

In some embodiments, negative pressure may be applied to the liquid-retention chamber 240 via a tube or other coupling 232 attached to the vacuum pump 234. When the vacuum source 230 is an internally-placed vacuum pump 234, the coupling 232 may travel from the pump 234 to the vacuum chamber 224 in gaseous communication with the liquid-retention chamber 240. When the vacuum source 230 is an internally-placed vacuum pump 234, an outlet 235 is provided for the vacuum pump to vent. The outlet may include a filter 237 to prevent germs from outside from entering inside or vice-versa. The opening of the coupling 232 in the vacuum chamber 224 may include a filter 261 (such as, in some embodiments, as antimicrobial filter) to prevent wound liquids from reaching the vacuum source 230 and to prevent any outside germs from entering the wound site. Moreover, in some embodiments the device 210 may include both inlet and outlet filters to prevent venting of microorganisms outside the housing 220.

In operation, the wound therapy device 210 may first be placed on a body surface of a patient so as to at least partially enclose a wound area. As discussed above, the device 210 may be sealed to the body surface using either just the suction generated by the device 210 alone, or using a seal 228 chosen from those known to those skilled in the art. The seal 228 illustrated in FIG. 6 is an adhesive seal covered during storage by a cover 216, optionally including a pull tab 218. The device 210 may further include a wound interface 241 as described herein.

Following attachment of the device 210 to a patient, the vacuum source 234 is activated, reducing the internal pressure of the device 210. As negative pressure is generated, liquids are drawn from the wound into the liquid-retention chamber 240 of the device 210, and are blocked from further progress into the vacuum chamber 224 or the negative pressure source 230 by the liquid barrier 236. As in the previous embodiments, the liquid barrier 236 may be any of those known to those of ordinary skill in the art, including, without limitation, porous hydrophobic films, and porous hydrophobic structures such as sponges and/or foams.

The exemplary device 210 of FIG. 6 further comprises a pressure relief valve 260 and a fill indicator 270. The pressure relief valve 260 may be used to maintain negative pressure within the internal space of the housing 220 (and thus within the liquid-retention chamber 240 and at the wound surface) at a therapeutic value. For example, Usupov et al. reported a therapeutic range of 75-80 mmHg to be desirable in their study with active wounds ("Active Wound Drainage", *Vestnik Khirurgii*, 1987, April pp 42-42). Alternatively, a differential pressure switch may be incorporated into the device 210 that will shut off the vacuum source 230 when the vacuum exceeds the desired negative pressure. Alternatively, a pressure sensor switch may be placed that shuts off the vacuum source 230 when the desired pressure is reached without any pressure relief valve.

The pressure relief valve 260 may additionally include an inflow filter (not shown) to prevent entry of contaminants into the device 210, and thus to further protect the wound site. The pressure relief valve 260 could operate in a variety of ways, including opening at a pre-set pressure point to allow ambient air to enter the device 210, opening the device 210 and deactivating the vacuum source 234, or simply deactivating the vacuum source 234.

The fill indicator 270 may operate in a variety of ways known to one of ordinary skill in the art. Some fill indicators 270 operate by detecting presence of free moisture in the liquid-retention chamber 240, which denotes that the porous pad has reached its absorptive capacity. Alternatively, fill indicator 270 may use electrical conductivity through a path in a portion of the liquid-retention chamber 240 to sense when moisture has reached the zone and provide a signal to shut off the vacuum source 230. Other fill indicators are known in the art and are suitable for use with the devices disclosed, including color-change technology based upon moisture content of the material or a change in a physical feature or characteristic. In some configurations, the fill indicator 270 may be coupled to an overflow valve to prevent wound liquids from reaching the vacuum pump 234.

Figure 7:
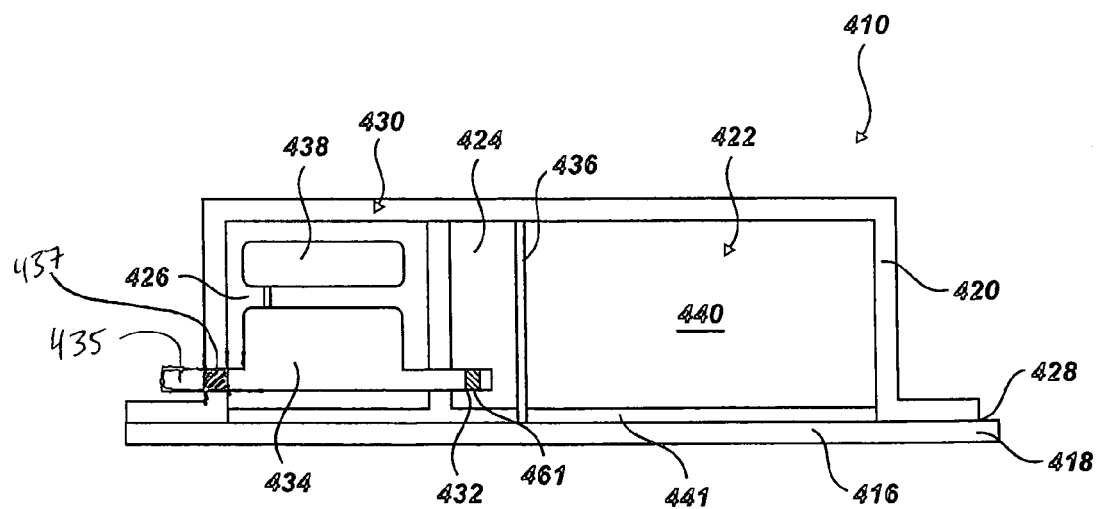
FIG. 7 is a side cross-sectional view of another alternative wound healing device including an internal vacuum pump as the vacuum source.

FIG. 7 illustrates yet another embodiment of a wound therapy device 410. Wound therapy device 410 offsets the vacuum source 434 and its associated power source 438 further from the wound site, which together may or may not be within the housing. In some situations, the offset may be beneficial for the wound. Similar to previous embodiments, the device 410 may include a housing 420 that encloses an internal space 422. This space 422 is subdivided into a vacuum chamber 424, a liquid-retention chamber 440, and an auxiliary chamber 426. As with previously-discussed embodiments, however, it is optional to include the auxiliary chamber 426, or to enclose the vacuum source 434 and power source 438 therein. When the vacuum source is an internally-placed vacuum pump 434, an outlet 435 is provided for the vacuum pump to vent. The outlet may include a filter 437 to prevent germs from outside from entering inside or vice-versa.

In this embodiment, the negative pressure source 430 extends through the housing 420 into the vacuum chamber 424 at an outlet 432. The outlet 432 may include a filter 461 (such as, in some embodiments, as antimicrobial filter) to prevent entry of wound exudate into the vacuum source 434. As with the other embodiments, this device 410 may include a liquid barrier 436, such as a hydrophobic membrane, that prevents flow of liquid into the vacuum chamber 424, but allows the negative pressure to extend into the liquid-retention chamber 440, causing liquid to be drawn into the liquid-retention chamber 440 from the wound. In some embodiments, the vacuum chamber 424 may include a porous hydrophobic foam. In other embodiments, the vacuum chamber 424 may be empty.

As described herein, the device 410 may be sealed to the body surface of a patient using either just the suction generated by the device 410 alone, or using a seal 428 chosen from those known to individuals skilled in the art. The seal 428 illustrated in FIG. 7 is an adhesive seal covered during storage by a cover 416, optionally including a pull tab 418. The device 410 may further include a wound interface 441 as similarly described herein.

Figure 8:
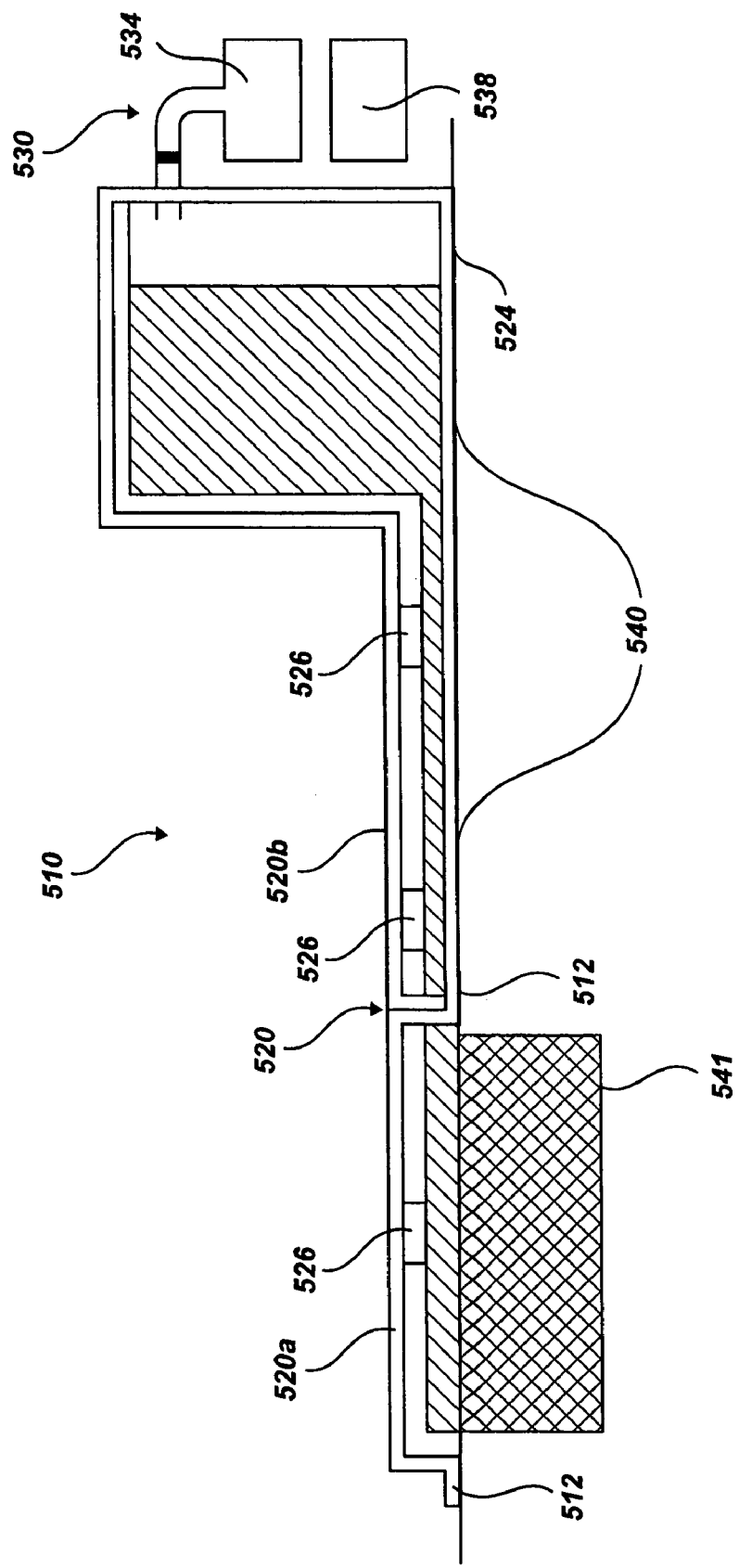
FIG. 8 is side cross-sectional view of another embodiment of a wound healing device with a housing of elongate shape.

FIG. 8 illustrates an alternative embodiment of a wound therapy device 510 that is applicable to assist in the healing of wounds located on parts of the body while standing, sitting, or laying, i.e., heel of the foot or buttock. In those instances it may be desirable that the wound site dressing and device components in the loaded areas substantially conform to the surrounding body so as to avoid pressure loading at the device site which may be detrimental to healing or could cause additional wounds. Furthermore, it may be desirable to collect wound liquid or exudate at a position remote from, but still adjacent the wound site.

To accomplish this, the device 510 shown in FIG. 8 has an elongated housing 520 structure where the wound interface 541 is located at the one end, and the negative pressure source 530 is located at the other end outside the housing 520. The liquid-retention chamber 540 extends from the wound interface 541 to the negative pressure source 530. In this embodiment a majority portion of the liquid-retention chamber 540 is at the end of the housing 520 adjacent the negative pressure source 530. The wound interface 541 located at the wound site seals the wound and allows application of negative pressure to the wound site. The wound interface 541 may be in contact with the liquid-retention chamber 540 which extends to the location of the vacuum supply chamber 524. This extended liquid-retention chamber 540 allows the placement of the negative pressure source at a different location compared to a wound site.

In one embodiment the liquid-retention chamber 540 is shaped such that the majority of wound fluid or exudate is collected at a location adjacent to the negative pressure source 530 and away from the wound site. In this instance, the liquid-retention chamber 540 may have a low aspect ratio at the wound site to minimize pressure loading as the patient sits, stands, or lies on the wound site.

Alternatively, the device 510 may have two separate housings: one housing 520*a* having a sealing surface 512 around the wound site and the other housing 520*b* being located at some distance away from the wound site. The latter housing 520*b* may or may not seal to the skin. Both housings 520*a*, 520*b* shown in FIG. 8 may be constructed of a liquid impermeable flexible barrier optionally supported by rigid or semi-rigid support structures 526. The housing 520*b* containing the vacuum chamber 524 may be located more conveniently where loading due to sitting, standing, or lying will not occur or can be substantially avoided.

The negative pressure source 530 may include a micro-vacuum pump 534 operably coupled to a power source 538, such as a battery. The negative pressure source 530 may be external to the housing 520, as illustrated. However, it should be understood that alternative embodiments of the wound therapy device 510 may include the micro-vacuum pump 534 and/or power source 538 internal to the housing 520. The negative pressure source 530 may be an osmotic or electroosmotic pump adjacent or internal to or adjacent the housing as discussed above.

Figure 9A:
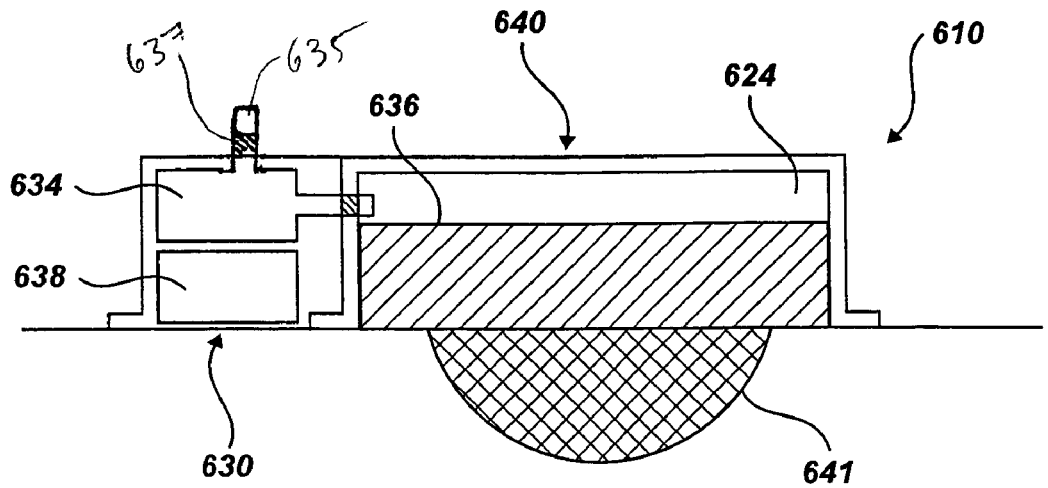
FIGS. 9A and 9B are schematic views of wound healing devices illustrating a modular approach to the device construction.
Figure 9B:
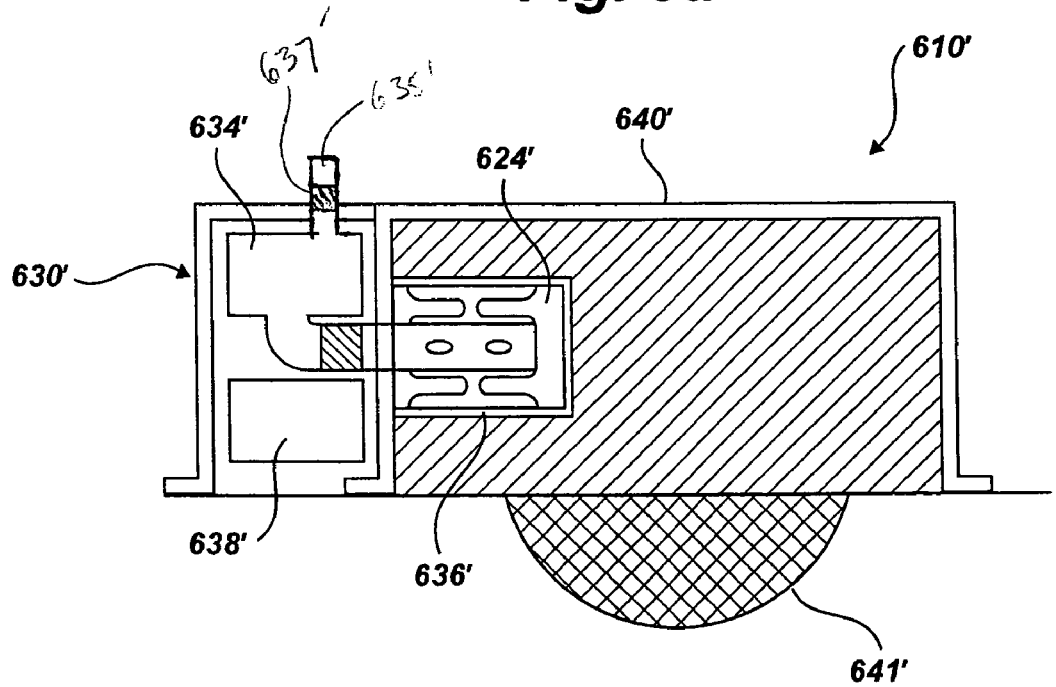

FIGS. 9A and 9B illustrate embodiments of a wound therapy device 610, 610' which are modular in nature. In this embodiment, the device 610, 610' may separate into three modules. However, greater or less than three modules may be used as would be apparent to one having skill in the art with the aid of the present disclosure. In the embodiments depicted, the device 610, 610' includes a wound interface module 641, 641', a liquid-retention module 640, 640', and a vacuum pump module 630, 630'. Due to its modular nature, any one of the modules of the device 610, 610' can be replaced as needed.

For example, if the liquid-retention module 640, 640' is filled to capacity with exudate, it may be replaced with a new liquid-retention module 640, 640', while keeping the functional vacuum pump module 630, 630'. Alternatively, the liquid-retention module 640, 640' may be replaced at regular intervals to prevent overflow and assure appropriate capacity. Likewise, the wound interface module 641, 641' may be replaced independent of the other modules.

In the embodiment of FIG. 9A, the liquid-retention module 640 is similar in design to the embodiments depicted in FIGS. 2 and 6. Whereas, the liquid-retention module 640' of FIG. 9B is similar in design to the embodiment depicted in FIGS. 3 and 4. Both embodiments of device 610, 610' include a liquid barrier 636, 636' to restrict exudate from entering into vacuum chamber 624, 624'. The vacuum pump module 630, 630' may include a vacuum source 634, 634', and optionally, a power source 638, 638'. When the vacuum source 634, 634' is internally placed, an outlet 635, 635' is provided for the vacuum source 634, 634' to vent. The outlet 635, 635' may include a filter 637, 637' to prevent germs from outside from entering inside or vice-versa.

The wound interface module 641, 641' of both embodiments may serve many functions as described above, such as being a layer that allows supply of vacuum to the wound while allowing easy and unpainful removal from the wound site during dressing changes. Alternatively, the wound interface may be a layer that provides beneficial bioagents in the form of specialized dressings such as dermal regeneration templates, bioabsorbable gels, foams and barriers that prevent tissue adhesion. The wound interface may also be a skin substitute, a layer for selectively maintaining moisture at the wound site, a layer that is angiogenic, and a layer that is antimicrobial. The wound interface may take a variety of forms, including, but not limited to a sheet, foam, gel, gauze or a porous matrix.

Figure 10:
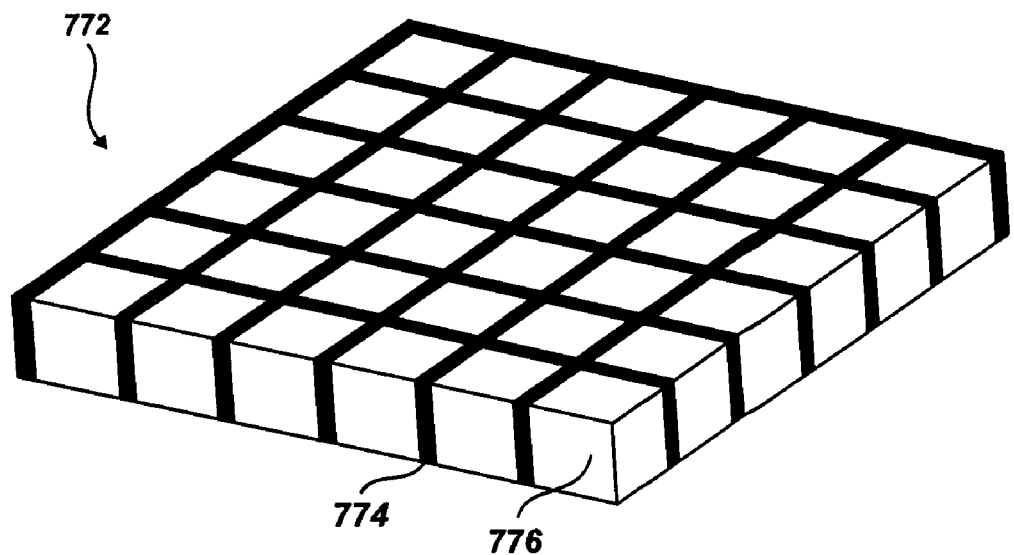
FIG. 10 is a perspective view of structural and absorbent material that may be disposed within a liquid retention chamber of a wound healing device.

FIG. 10 illustrates support structure 772 that may be disposed within the liquid retention chamber of a wound therapy device. The support structure 772 may be shaped and/or customized to fit within the wound therapy device. The support structure 772 may include a structural support material 774 that is configured to provide support for the wound therapy device housing while under a negative pressure. The structural support material 774 may be constructed from rigid or semi-rigid plastics and the like. Disposed between the structural support material 774 is an absorbent material 776 for absorbing and retaining wound exudate within the liquid retention chamber. As described above, the absorbent material 776 may include sponges; wicking fibers, fabrics or gauzes; super-absorbent material including super-absorbent polymers; absorbent foams; gelling agents; packing and the like. In some embodiments, the absorbent material 776 may also serve as structural supports to the housing while the wound therapy device is under a negative pressure.

Figure 11:
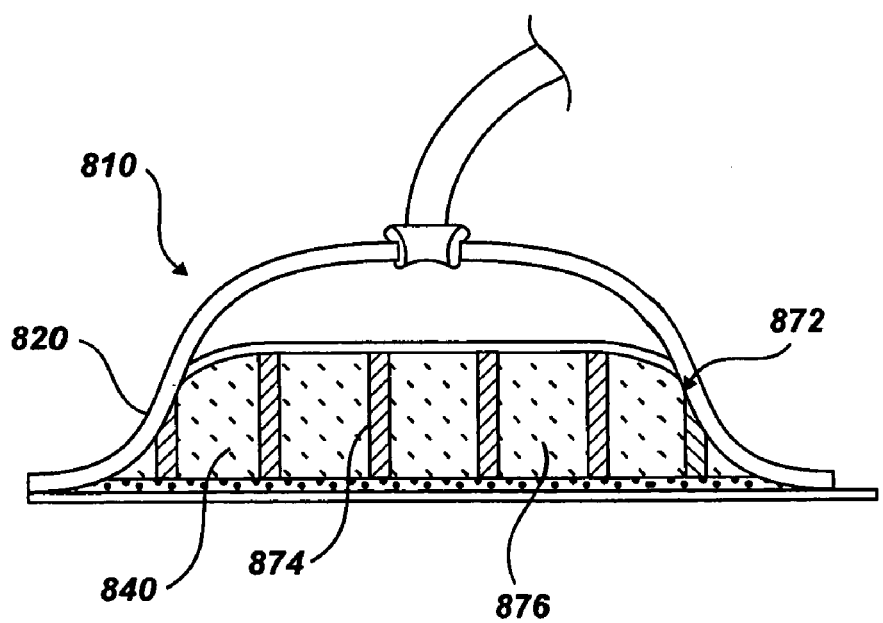
FIG. 11 is a side cross-sectional view of another embodiment of a wound healing device.

FIG. 11 represents another embodiment of a wound therapy device 810, similar to the embodiment depicted and described in conjunction with FIG. 2. The wound therapy device 810 may include a support structure 872 within the housing 820. As described in FIG. 10, the support structure 872 may include a structural support material 874 and an absorbent material 876 disposed within the liquid retention chamber 840.

Without limitation, it is believed that the disclosed devices and their methods of use may be useful for the therapy of surface wounds on a patient. These wounds may include, but are not limited to, infectious wounds, burn wounds, venous and arterial ulcers, diabetic ulcers and wounds, post-surgical wounds, bed sore wounds, and the like. Additionally, such devices are contemplated for use in a variety of fields, as would be contemplated by one of ordinary skill in the art.

According to one method of wound treatment or therapy utilizing the devices described herein, a device having a housing with a liquid-retention chamber is positioned above at least a portion of the wound. Negative pressure may be applied to the wound using the vacuum source. Wound liquids or exudate may be collected in the liquid-retention chamber.

Additionally, the device may be replaced when it is filled with liquid. In modular embodiments, the liquid-retention chamber or the vacuum source may be replaced as needed.

In some of the embodiments disclosed, the devices may be adapted to be inexpensive, light-weight, and either partially or entirely disposable. Further, the devices may be adapted to be simple to operate, such that in some instances, a patient could place the device with some reduced degree of medical supervision. In addition to the above, the devices may be constructed so as to be used without attention to their orientation.

It is contemplated that the devices may take a variety of forms, including those that are completely disposable when full, or partially disposable such as, for example, either the vacuum source or the liquid-retention chamber. In embodiments such as device 10 of FIGS. 1 and 2, it may be that the entire device may be discarded and replaced when filled. This may be convenient for smaller wounds, wounds that are already well along in the healing process, and wounds that are under home care. Such methods and apparatus prevent and/or reduce contact with potentially contagious or dangerous bodily liquids.

Such methods and apparatus may also be useful in the treatment of skin grafts. Additionally, such a device may be useful when applying sub-dermal materials, such as dermal regeneration templates, intended to serve as a matrix for tissue to enter in the healing process of burns and wounds.

It should be noted that although the housings disclosed have been illustrated in particular shapes, such as being generally rounded, the housings are not necessarily limited to particular shape, and may be constructed in any advantageous shape. In some embodiments, the devices may be sized and shaped such that the vacuum chamber or liquid-retention chamber is capable of sealing over the patient's wound, at least in part. The housings and the seals disclosed may be configured to hold a vacuum when the device is placed and sealed over at least a portion of a wound on a patient's body surface. Such seals may be substantially airtight to prevent the entry of microbes but do not need to be absolutely impermeable. Although it is contemplated that vacuum pressure will either be continuously or periodically applied to maintain a therapeutic negative pressure therapy range.

Power sources referred to herein may be, for example, electrical outlets, batteries, and/or rechargeable batteries and the like. By way of example, the batteries may be integral (non-replaceable), replaceable (by a user or clinician) and/or rechargeable.

When the vacuum is switched on after placing the device on a patient's wound, air is removed around the wound, generating a vacuum within the housing cavity. At the same time, wound-liquid absorbing material may begin absorbing the exudate/liquids in the wound. Sustained negative pressure over a wound region may promote tissue migration and wound closure. In some embodiments, the devices may be shaped like a patch or bandage that may be changed more than once a day.

Additionally, the device may contain a fill indicator that senses the presence of free moisture in the liquid-retention chamber that signals that the optional porous pad has reached its absorptive capacity. The fill indicator may in turn be coupled to an over-flow valve to prevent wound liquids from reaching the vacuum pump or it may provide a signal used to prompt disabling the pump.

In all of the above embodiments, when the devices are adapted to be disposable, they may be discarded after use in part or in whole. Indeed multiple disposable devices can be provided to a patient for a treatment plan, which may consist of a plurality of individual treatments with disposable devices over a predetermined period.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. § 112 ¶6. The scope of the invention is therefore defined by the following claims.

The invention claimed is:

1. A wound therapy device, comprising:
   a housing to cover at least a portion of a wound site;
   a liquid retention chamber position within the housing, wherein the liquid retention chamber collects and stores at least one of liquid exudate and bodily fluid from the wound site, and, wherein the liquid retention chamber retains the collected liquid exudate and bodily fluid stored therein upon application of negative pressure thereto;
   an opening in the housing operatively associated with a vacuum source for creating negative pressure within at least the liquid retention chamber; and,
   a gas permeable liquid barrier associated with the housing for precluding migration of the liquid exudate and bodily fluid into and through the opening and into the vacuum source.

2. The wound therapy device of claim 1, further comprising a seal for sealing the housing to a body surface of a patient.

3. The wound therapy device of claim 1, wherein the housing is constructed of a material having a rigidity sufficient to prevent significant collapse of the liquid retention chamber when subject to a pressure lower than atmospheric pressure.

4. The wound therapy device of claim 3, wherein the housing material is chosen from a rigid plastic, semi rigid plastic, rigid rubber, semi rigid rubber and combinations thereof.

5. The wound therapy device of claim 1, wherein the housing comprises a flexible baffler.

6. The wound therapy device of claim 1, further comprising:
   structural supports to prevent significant collapse of the liquid-retention chamber when subject to a pressure lower than atmospheric pressure.

7. The wound therapy device of claim 6, wherein the structural supports provide support to the housing, and the structural supports are chosen from: customizable rigid and customizable semi-rigid structural supports.

8. The wound therapy device of claim 1, further comprising structural foam within the liquid-retention chamber to prevent significant collapse of the liquid-retention chamber when subject to a pressure lower than atmospheric pressure.

9. The wound therapy device of claim 1, wherein the liquid baffler is chosen from: porous polytetrafluoroethylene, microporous polytetrafluoroethylene, porous polypropylene, microporous polypropylene, porous polyethylene, microporous polyethylene, and combinations thereof.

10. The wound therapy device of claim 1, wherein the liquid barrier is a labyrinth.

11. The wound therapy device of claim 1, wherein the liquid barrier is a droplet gap.

12. The wound therapy device of claim 1, wherein the liquid retention chamber further comprises a porous structure for retaining liquid.

13. The wound therapy device of claim 12, wherein the porous structure is chosen from: a sponge, packing material, a gelling agent, a super-absorbent polymer material and combinations thereof.

14. The wound therapy device of claim 1, wherein the liquid retention chamber further comprises an antimicrobial agent.

15. The wound therapy device of claim 1, wherein the opening comprises a vacuum port configured to be coupled to a vacuum supply line.

16. The wound therapy device of claim 1, wherein the opening is coupled to a micro-vacuum pump disposed adjacent the wound.

17. The wound therapy device of claim 1, further comprising a pressure relief valve to maintain pressure within the housing.

18. The wound therapy device of claim 17, wherein the pressure relief valve further comprises an inflow filter.

19. The wound therapy device of claim 1, wherein a pressure inside the housing is controlled by a switch that deactivates the vacuum source below a lower negative pressure threshold.

20. The wound therapy device of claim 19, wherein the switch further activates the vacuum source above an upper negative pressure threshold.

21. The wound therapy device of claim 1, further comprising a fill indicator.

22. The wound therapy device of claim 21, wherein the fill indicator provides a signal that prompts a deactivation of the vacuum source.

23. The wound therapy device of claim 1, further comprising an overflow valve.

24. The wound therapy device of claim 1, wherein the housing is constructed of plastic chosen from: polypropylene, polyurethane, polyvinyl chlorides, polyethylene, acrylonitrile copolymers, nylon, polyester, polychlorotrifluoroethylene, fluoropolymer, and polytetrafluoroethylene and combinations thereof.

25. The wound therapy device of claim 1, further comprising a wound interface layer.

26. The wound therapy device of claim 25, wherein the wound interface layer comprises multiple layers.

27. The wound therapy device of claim 25, wherein the wound interface layer is configured to be disposed adjacent the wound.

28. The wound therapy device of claim 25, wherein the wound interface layer is at least one of the following: a degradable copolymer foil, dermal regeneration templates, bioabsorbable gels, bioabsorbable foams, tissue adhesion prevention bafflers, a skin substitute, a layer that selectively maintains moisture, an angiogenic layer, and an antimicrobial layer.

29. The wound therapy device of claim 1, wherein the housing is semi-permeable.

30. The wound therapy device of claim 29, wherein the semi-permeable housing has a water vapor transmission rate of greater than about $836/m^2 day$.

* * * * *

UNITED STATES PATENT AND TRADEMARK OFFICE
CERTIFICATE OF CORRECTION

PATENT NO. : 7,615,036 B2  
APPLICATION NO. : 11/432855  
DATED : November 10, 2009  
INVENTOR(S) : Ashok V. Joshi Page 1 of 1

It is certified that error appears in the above-identified patent and that said Letters Patent is hereby corrected as shown below:

On the Title Page

In column 2 (page 2, item 56) at line 35, Under Other Publications, change "Vaccuum" to --Vacuum--.

In the Specification

In column 4 at line 38, Change "an/or" to --and/or--.

In column 5 at line 32, Change "Alevyn®" to --Allevyn®--.

In the Claims

In column 12 at line 47, In Claim 5, change "baffler." to --barrier.--.

In column 12 at line 62, In Claim 9, change "baffler" to --barrier--.

In column 14 at line 23, In Claim 28, change "bafflers," to --barriers,--.

Signed and Sealed this  
Sixteenth Day of June, 2015

Michelle K. Lee  
*Director of the United States Patent and Trademark Office*